United States Patent
Mu

(10) Patent No.: US 9,395,449 B2
(45) Date of Patent: Jul. 19, 2016

(54) POSITRON EMISSION TOMOGRAPHY IMAGING METHOD AND SYSTEM

(71) Applicant: Zhiping Mu, Chongqing (CN)

(72) Inventor: Zhiping Mu, Chongqing (CN)

(*) Notice: Subject to any disclaimer, the term of this patent is extended or adjusted under 35 U.S.C. 154(b) by 385 days.

(21) Appl. No.: 13/865,727

(22) Filed: Apr. 18, 2013

(65) Prior Publication Data

US 2013/0299705 A1 Nov. 14, 2013

Related U.S. Application Data

(63) Continuation of application No. PCT/CN2011/080998, filed on Oct. 19, 2011.

(30) Foreign Application Priority Data

Oct. 21, 2010 (CN) .......................... 2010 1 0514670

(51) Int. Cl.
*G01T 1/16* (2006.01)
*G01T 1/166* (2006.01)
(Continued)

(52) U.S. Cl.
CPC .............. *G01T 1/1663* (2013.01); *A61B 6/037* (2013.01); *G06T 11/006* (2013.01); *G06T 2211/424* (2013.01)

(58) Field of Classification Search
CPC .... G01T 1/1663; A61B 6/037; G06T 11/006; G06T 2211/424
See application file for complete search history.

(56) References Cited

U.S. PATENT DOCUMENTS

| 7,381,960 B1* | 6/2008 | Chuang ................. G01T 1/1603 250/363.03 |
| 7,968,852 B1* | 6/2011 | Malmin et al. ........... 250/370.09 |
| 2009/0256078 A1* | 10/2009 | Mazin ................... G01T 1/2985 250/362 |

(Continued)

FOREIGN PATENT DOCUMENTS

| CN | 101964115 A | 2/2011 |
| WO | WO 2006/120605 | * 11/2006 |

OTHER PUBLICATIONS

Zhiping Mu et al., A novel three-dimensional image reconstruction method for near-field coded aperture single photon emission computerized tomography, Am. Assoc. Phys. Med., 2009, p. 1533-1542, vol. 36, No. 5.

(Continued)

*Primary Examiner* — Yara B Green
(74) *Attorney, Agent, or Firm* — Locke Lord LLP; Tim Tingkang Xia, Esq.

(57) ABSTRACT

The technical solution as put forth by the present invention comprises a computer imaging system and detectors arranged around the detected object for collecting gamma photons from positron annihilation events. The key is a multi-pinhole plate placed between the detected object and the detectors, and the multi-pinhole plate can be a coded aperture mask coded by using a function h(x,y). The gamma photons generated from the annihilation events inside the detected object are absorbed by the detector after being collimated by the multi-pinhole plate. Accordingly, after the detectors have performed detection at multiple angles, the result is transmitted to the computer imaging system, and quasi three-dimensional images are generated after being processed by the disclosed algorithm. Furthermore, the quasi three-dimensional images generate secondary projection images and, after adjustment, generate sinograms, and finally three-dimensional tomographic images are reconstructed from multiple sinograms.

18 Claims, 2 Drawing Sheets

(51) Int. Cl.
*A61B 6/03* (2006.01)
*G06T 11/00* (2006.01)

(56) References Cited

U.S. PATENT DOCUMENTS

| | | | |
|---|---|---|---|
| 2010/0080339 A1 | 4/2010 | Austin et al. | |
| 2010/0219347 A1* | 9/2010 | Schulz | G01T 1/1603 250/363.04 |
| 2010/0294941 A1* | 11/2010 | Chuang | A61B 6/037 250/363.04 |
| 2011/0089326 A1* | 4/2011 | Falen et al. | 250/363.04 |
| 2011/0190616 A1* | 8/2011 | Marwala et al. | 600/407 |
| 2011/0251478 A1* | 10/2011 | Wieczorek | A61B 5/1127 600/411 |
| 2012/0056095 A1* | 3/2012 | Metzler | G21K 1/025 250/363.1 |

OTHER PUBLICATIONS

Zhiping Mu et al., Aperture Collimation Correction and Maximum-Likelihood Image Reconstruction for Near-Field Coded Aperture Imaging of Single Photon Emission Computerized Tomography, IEEE Transactions on Medical Imaging, 2006, p. 701-711, vol. 25, No. 6.

\* cited by examiner

POSITRON EMISSION TOMOGRAPHY IMAGING METHOD AND SYSTEM

CROSS-REFERENCE TO RELATED APPLICATIONS

This application is a continuation of International Patent Application No. PCT/CN2011/080998, with an international filing date of Oct. 19, 2011, designating the United States, now pending, which is based on Chinese Patent Application No. 201010514670.7, filed Oct. 21, 2010. The contents of these specifications are incorporated herein by reference.

BACKGROUND OF THE INVENTION

1. Field of the Invention

The present invention relates to methods and systems that detect gamma rays and reconstruct images, and particularly a technical solution that is applied to medical positron emission tomography (PET) equipment to acquire an image of a target position of a human body.

2. Description of the Related Art

PET is an important modern medical imaging technology used in the diagnosis of many diseases such as tumor and Alzheimer disease. A detected object is traced by a radioactive isotope (such as F-18) of β+ decay. β+ particles (also known positrons) emitted by the isotope collide with electrons within the detected object, causing annihilation and producing a pair of 511 keV gamma photons traveling along approximately opposite directions. Current clinical PET scanners are equipped with a detector system deployed in the form of a cylindrical array. In general, if the detector system detects a pair of 511 keV gamma photons within a very short time window by using a time coupling circuit, the system considers an annihilation event occurred somewhere on the line connecting the pair of gamma photons. This process is called time coupling, and also referred to as electronic collimation.

Objectively, the time coupling technology eliminates the need for collimation devices, improving the efficiency in counting of individual gamma photons. However, if multiple annihilation events occur within a short period of time and more than two 511 keV gamma photons are detected within the short time window, the system cannot determine in which line the event occurred, causing errors. If only one gamma photon is detected, there is no way to determine its traveling path, and thus this photon count can not be used for reconstruction. Additionally, time coupling usually requires using layers of detectors arranged in a ring shape, and uses a scintillator with a short light emission decay time, such as lutetium oxyorthosilicate (LSO), and fast-responsive electronic circuits and photomultiplier tubes (PMTS), pushing high the cost of PET systems. More importantly, the detectors in PET provide only a small spatial coverage, but annihilation photons could travel in any directions, resulting in a very low effective coupling ratio, i.e. when one detector detects a 511 keV gamma photon, the chance of one and only one other detector detecting a 511 keV gamma photon within timing-window is very low. That is because there is a high probability that the other gamma photon (generated from the same annihilation event) flies out of the area which the detector system covers, or the other gamma photon passes through a detector but is not detected due to the limited detecting efficiency. It has been reported that the effective coupled count is only 1-2% of the individual gamma photon count. This number includes some random coupling.

In astronomy, the coded aperture imaging technology is applied, which detects gamma rays emitted from celestial bodies using a coded aperture mask. A coded aperture collimation device is disposed between a detector and the measured space while collecting images, and the collimation device is parallel with the detector array. Gamma photons emitted from a point-shape celestial body travel through small openings of the coded aperture mask, and project onto the surface of detector array, forming a shadow matching the pattern of the small openings on the coded aperture mask. Because the distance from celestial body to the coded aperture mask is extremely long, the gamma photons emitted from the same celestial body are considered traveling in the same direction, namely the far field imaging. It is generally deemed impossible to apply this technology into near filed imaging such as medical imaging.

SUMMARY OF THE INVENTION

An objective of the present invention is to provide a PET imaging method. The method discloses a multi-pinhole plate design. This method is capable of acquiring a clear quasi three-dimensional image or a full three-dimensional image. In addition, the design of the multi-pinhole plate provides a collimation method for photon detection, which allows image to be acquired by detecting individual gamma photons (without time coupling). If applied to imaging systems, the method allows more freedom in detector arrangement (allows for non-ring shape design). With this method, a scintillator with a short light emission decay time, and a fast-responsive electronic circuit and photomultiplier tubes may not be used any longer, thereby eliminating the need for the expensive time coupling electronic circuits.

Another objective of the present invention is to provide a PET imaging system. The system employs a collimation method for near field imaging using multi-pinhole plate described above. The system cost is significantly lowered as compared with the prior art.

The technical solution to achieve the objective of the present invention is as follows: a PET imaging method is provided, wherein involved equipment includes a computer imaging system, a device carrying a detected object, and a detector system disposed around the detected object for collecting gamma photons emitted in a positron annihilation event; wherein a multi-pinhole plate is disposed between the detected object and a detector, and the detected object is traced by a radioactive isotope of β+ decay; the imaging method includes the following steps: 1) collecting, by the detector, gamma photon projections from a plurality of angles, a projection image is denoted by p(x, y), where x and y denote a two-dimensional coordinate of the detector; 2) reconstructing a three-dimensional image based on all the projection images.

In the method mentioned above, the detector system may be detectors disposed in a planar array, and x and y denote a two-dimensional coordinate within the detector plane respectively. The detector system may be deployed in other configurations, but still uses x and y to denote the coordinate thereof. Understandably, to facilitate processing, the detector system coordinate may also be transformed in such a way that it is equivalent to multiple planar detector arrays. Tracer isotopes may be drugs capable of generating positrons by triggering β+ decay. Tracer marking is made to a detected object as required before detection. The design of the multi-pinhole plate can allow acquisition of an image by detection of individual gamma photons. Therefore, there is no need for the time-coupling system that determines the coincidence of two gamma photons and therefore the path of annihilation event, improving both detection accuracy and post processing efficiency. Furthermore, every gamma photon emitted from annihilation can be used for imaging, yielding higher detecting accuracy. Because no time-coupling is performed, even if a plurality of gamma photons are detected within a short time window, errors as occurred in conventional systems will not be present. In the method provided in the present invention, the computer imaging system, detected object, the device for carrying a detected object, and the detector components in conventional PET equipment can still be used without modifications. In addition, in systems upgraded using this method, the detectors does not need to be arranged in ring shapes, there is no time coupling electronic circuits, it is no longer imperative to use scintillators with a short light emission decay time, and fast-responsive electronic circuits and photomultiplier tubes, significantly reducing the cost.

In the technical solutions disclosed in the present invention, the multi-pinhole plate is operable to collimate gamma photons. The gamma photon pass rate at the open pinholes on the multi-pinhole plate or the coded aperture mask is at least 50% higher than in an area without open holes. Therefore, the holes could be covered or filled by other material that has less attenuating effect than the plate material.

The present invention also provides a PET imaging system, including: a computer imaging system, a device carrying a detected object, and a detector system disposed around the detected object for collecting gamma photons emitted in a positron annihilation event; wherein the detected object is traced by a radioactive isotope of β+ decay, and a multi-pinhole plate is disposed between the detected object and a detector.

The design of the multi-pinhole plate provides a collimation method for imaging equipment so that individual photons count can be used for imaging, rather than photon pairs that are considered coincident by the time coupling circuits in conventional PET systems. Similar to the method introduced in the present invention, in the system, components such as computer imaging system, the device for carrying a detected object, and the detector components in conventional PET systems can still be used without modifications. In particular, the detectors do not need to be disposed in a ring shape, significantly lowering the system cost.

BRIEF DESCRIPTION OF THE DRAWINGS

The present invention is further illustrated with reference to the exemplary embodiments illustrated in the drawings, among which.

Figure 1:
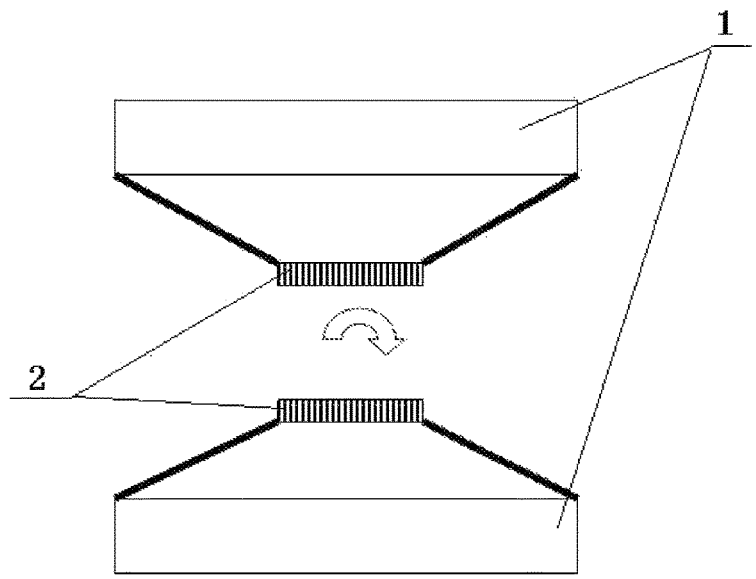
FIG. 1 is a schematic diagram of modules in a detector system according to the present invention.
Figure 2:
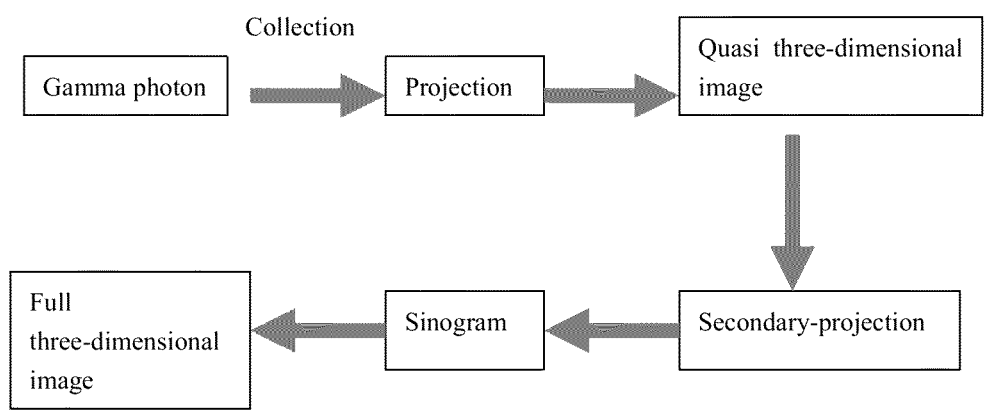
FIG. 2 is a flowchart according to the present invention.
Figure 3:
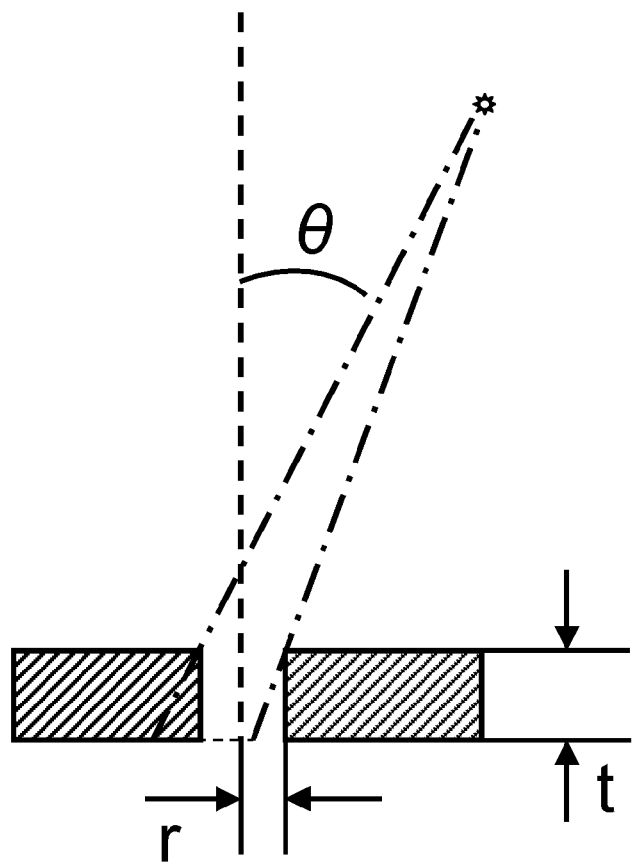
FIG. 3 is schematic diagram of a coded aperture according to the present invention.

In the drawing, 1 denotes a detector, and 2 denotes a multi-pinhole plate.

DETAILED DESCRIPTION OF THE EMBODIMENTS

The following further describes the present invention with reference to specific embodiments. However, the scope of the subject matter of the present invention is not limited to such specific embodiments. Various replacements and variations made according to common technical knowledge and common technical means in the art without departing from the technical concept of the present invention all fall within the scope of the present invention.

Embodiment One

A PET imaging method is disclosed, wherein involved equipment includes a computer imaging system, a device carrying a detected object, and a detector system disposed, as a planar array, around the detected object for collecting gamma photons emitted in a positron annihilation event; wherein a multi-pinhole plate is disposed between the detected object and a detector, and the detected object is traced by a radioactive isotope of β+ decay. The imaging method includes the following steps: 1) collecting, by the detector, gamma photon projections from a plurality of angles, a projection image is denoted by p(x, y), where x and y denote a two-dimensional coordinate of the detector in the detector plane; and 2) reconstructing a three-dimensional image based on all the projection images.

Generally, three-dimensional images can be reconstructed using the well-known maximum likelihood expectation maximization (MLEM) algorithm:

$$\hat{f}_j^{(k+1)} = \frac{\hat{f}_j^{(K)}}{\sum_{i=1}^{I} K_{ij}} \sum_{i=1}^{I} \frac{p_i K_{ij}}{\sum_{i=1}^{I} K_{ij} \hat{f}_j^{(K)}},$$

where i denotes a location of the $i^{th}$ detector, a combination of (x, y, θ) of a projection image p; j denotes the $j^{th}$ location of the detected object, also a three-dimensional coordinate of (x, y, z); I denotes the total number of detector locations; J denotes the total number of locations of the detected objects; $\hat{f}_j^{(k)}$ denotes the $k^{th}$ estimation at the location j (of a three-dimensional image) of the detected object; $K_{ij}$ denotes a detection probability matrix, a probability that gamma photons emitted from location j of the detected object is detected by a detector at location i; $K_{ij}$ can be acquired by experimental detection.

Embodiment Two

According to the PET method provided in Embodiment 1, in this embodiment, the multi-pinhole plate is a planar plate, wherein the number of pinholes thereon is larger than 10, and is a coded aperture mask coded by using a function h(x, y). The function h has a range of 0 or 1, where, 0 denotes a blind or closed hole, i.e., a hole which is difficult for gamma photons to pass through; 1 denotes a through or open hole, i.e., a hole which is easy for gamma photons to pass through as compared against blind holes.

In the meantime, another processing matrix function g(x, y) matching h(x, y) exists, and a relationship between the two functions is denoted by an equation h(x, y)⊗g(x, y)=δ(x, y), where δ(x, y) denotes a delta matrix function, ⊗ denotes a correlation operation; and during the image collecting in step 1), the detector detects the projections from the plurality of angles, and the projection is denoted by p(x, y, θ), where θ denotes an angle and is used as a mark.

In this example, to achieve a better imaging effect, the detector collects projections from more than eight angles.

Furthermore, the number of holes disposed on the multi-pinhole plate is larger than 10, such that more gamma photons pass through the multi-pinhole plate, thereby improving sensitivity of the equipment adopting the method.

Figure 4:
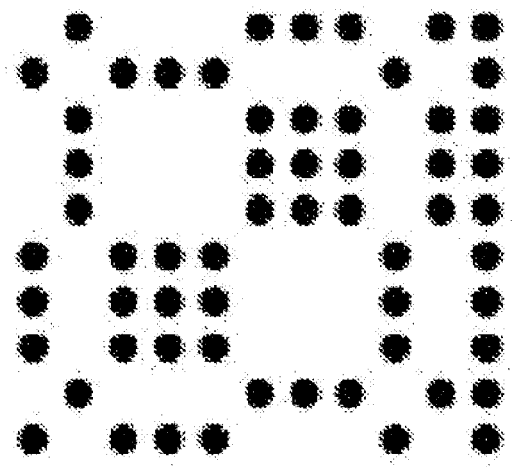
FIG. 4 illustrates a No-Two-Hole-Touching modified uniformly redundant array (NTHT MURA) coded aperture mask.

The coded aperture mask may be designed in a plurality of manners. Typically, the coded aperture mask is designed by using No-Two-Holes-Touching modified uniformly redundant array (NTHT MURA), a uniformly redundant array (URA), a random array or a pseudo random array. FIG. 4 is an illustration of a coded aperture mask designed by using an NTHT MURA.

Embodiment Three

In Embodiments 1 and 2, the three-dimensional image is reconstructed using the method in the prior art. This embodiment, based on the description given in the above two embodiments, further describes the method for reconstructing the three-dimensional image.

In the method disclosed in the present invention, reconstructing a three-dimensional image in step 2) includes the following steps:

A. performing operations in steps a) and b) on each of the collected projection images:
  a) generation of a quasi three-dimensional image: dividing the detected object into n layers, where n≥3, and z is a distance (i.e., depth) from each layer to the detector; and acquiring a quasi three-dimensional image of the detected object by using an iterative algorithm;
  b) generation of a secondary projection image: adjusting image pixels on each layer to the same size by interpolation, where the image on each layer after adjustment is denoted by $f_{(1)}(x, y, z)$; the secondary projection image is denoted by $p_{(2)}(x, y)$, where the function is obtained by using the formula $$p_{(2)}(x,y)=\Sigma_z f_{(1)}(x,y,z).$$

B. generating a sinogram: extracting corresponding rows of each cross section from each secondary projection image, and generating the sinogram by arrangement according to the collection angles; and C. generating a full three-dimensional image: reconstructing a tomography for each cross section from each sinogram.

In the aforementioned operation a), a quasi three-dimensional image can be acquired from a individual projection image by using the following well-known algorithm:

$$f_L(x,y,z)=p(x,y)\otimes g_z(x,y),$$

where $f_L(x, y, z)$ denotes the quasi three-dimensional image to be generated, h(x, y, z) denotes a coded aperture mask projection corresponding to an object at a depth of z, $g_z(x, y)$ denotes a processing matrix matching h(x, y, z). This simple processing-based quasi three-dimensional reconstruction algorithm is also referred to as laminography.

Preferably, in addition to commonly used algorithms, in step a) in this embodiment, the following iterative algorithm may also be used:

$$\hat{f}^{(k+1)}(x, y, z) = \frac{\hat{f}^{(k)}(x, y, z)}{\sum_z h(x, y, z)} \left\{ h(x, y, z) \otimes \frac{p(x, y) - \sum_{z' \neq z}\left[\hat{f}^{(k)}(x, y, z') * h(x, y, z')\right]}{\hat{f}^{(k)}(x, y, z) * h(x, y, z)} \right\},$$

where k denotes the number of iterations, $\hat{f}^{(k)}(x, y, z)$ denotes the $k^{th}$ estimation of the detected object, h (x, y, z) denotes a coded aperture mask projection corresponding to an object at a depth of z, z denotes a distance from the detector to each layer, z' denotes a distance from the detector to another layer except the layer z, ⊗ denotes a correlation operation, and * denotes a convolution operation.

With the algorithm provided in the present invention above, image pixel size may be adjusted by interpolation. The pixel size on each layer of image is defined by a formula: q(z)=(z/b-1)d, where q(z) denotes a pixel size of a layer of image having a depth z, d denotes a pixel size of an acquired projection image p(x, y), b denotes the distance from the detector to the coded aperture mask. The adjusted pixel size usually is the pixel size of the layer of image closest to the detector. In the above steps, no limitation is set on reconstruction of a tomographic image from a sinogram. A preferred method, such as ordered subset expectation and maximization (OSEM), filtered back-projection (FBP), MLEM or Algebraic Reconstruction Technique, may be used to reconstruct the tomographic image from the sinogram.

Embodiment Four

Corresponding to the method disclosed in the present invention, a PET imaging system is disclosed in the present invention. The imaging system is capable of implementing the method as described in Embodiments 1 to 3. The system includes: a computer imaging system, a device carrying a detected object, and a detector system disposed around the detected object for collecting gamma photons emitted in a positron annihilation event; wherein the detected object is traced by a radioactive isotope of β+ decay, and a multi-pinhole plate is disposed between the detected object and a detector.

Furthermore, in this embodiment, the detector synchronously rotates with the multi-pinhole plate, thereby preventing impact on imaging due to relative motion of the detector against the multi-pinhole plate.

The multi-pinhole plate is a planar plate having a plurality of coded apertures, wherein a location of the coded apertures on the multi-pinhole plate is denoted by a matrix function. The detector rotates or is disposed at different angles to detect projections from a plurality of angles. The computer imaging system reconstructs a three-dimensional image based on the projections collected by the detector.

During image reconstruction, angular sensitivity of the detector, including an effective cross-section and a collimation effect, needs to be compensated, i.e., elimination of artifacts. The radius r of the aforementioned coded aperture is from 1.25 mm to 8 mm, the length t there of is from 3 mm to 20 mm.

Because β+ particles emitted by isotope collide with electrons in the detected object, resulting in annihilation and producing 511 keV gamma photons, the radius r of the coded aperture may be from 1.25 mm to 8 mm, the length t thereof may be from 3 mm to 20 mm. In application of the coded aperture mask technology into near field imaging, such as medical imaging, images are usually affected by angular artifacts. For better elimination of artifacts, the collected projection image should be compensated by distribution of detector angular sensitivity, S(α), where α is an incident angle of gamma photons. The detector angular sensitivity distribution includes two parts: the effective area of pinhole cross section and the collimation effect caused by hole thickness. Angular distribution of the effective area on the pinhole cross section includes angular projection (cos(α)) and increase of a distance from an object to the pinhole with the increase of the angle ($\cos^2(\alpha)$), i.e., a combined factor of $\cos^3(\alpha)$. The collimation effect of the hole thickness is caused by absorption and blockage of the gamma photons incident from an inclined angle. The formula for compensation is:

$$p_c(x,y)=p(x,y)/S(\alpha),$$

where $p_c(x, y)$ denotes a projection after compensation, and will be used as corrected $p(x, y)$ for reconstruction.

In the system disclosed in the present invention, the requirement for detector is relatively low since no time coupling is needed. It is not imperative to use a scintillator detector with a short light emission decay time. The detector in this embodiment may be a bismuth germanate (BGO)-based detector, a sodium iodide (NaI)-based detector, or a cesium iodide (CsI)-based detector.

In this embodiment, the multi-pinhole plate is made of a heavy metal, such as tungsten, lead, platinum or alloy thereof.

What is claimed is:

1. A method of positron emission tomography (PET) imaging; wherein the method is performed by an equipment and the equipment comprises a computer imaging system, a device carrying a detected object and a detector system disposed around the detected object for collecting gamma photons emitted in a positron annihilation event; wherein a multi-pinhole plate is disposed between the detected object and a detector, and the detected object is traced by a radioactive isotope of β+ decay; wherein the multi-pinhole plate is configured to collimate gamma photons, which allows an image to be acquired by detecting individual gamma photons emitted from annihilations without requirement to detect another photon coincident in time via a time coupling electronic circuit; the imaging method comprising the following steps:
    step 1), collecting, by the detector, gamma photon projections from a plurality of angles through the multi-pinhole plate, for generating a projection image which is denoted by p(x, y), wherein the x and y denote a coordinate of two dimensions of the detector, and a value of p represents photon counts detected by that detector individually without coincidence via the time coupling electronic circuit; and
    step 2), reconstructing, by the computer imaging system, a three-dimensional image based on all the projection images.

2. The method of claim 1, wherein the multi-pinhole plate is a planar plate, and is a coded aperture mask coded by using a function h(x, y), wherein a value of the function h(x, y) is 0 or 1; another processing matrix function g(x, y) matching the function h(x, y) exists, and a relationship between the two functions is denoted by an equation $h(x, y) \otimes g(x, y)=\delta(x, y)$, where $\delta(x, y)$ denotes a delta matrix function, $\otimes$ denotes a correlation operation; and
    during the image collecting in step 1), the detector detects the projections from the plurality of angles, and each of the projections is denoted by p(x, y, θ), where θ denotes an angle and is used as a mark.

3. The PET imaging method of claim 2, wherein the number of pinholes on the multi-pinhole plate is larger than 10.

4. The PET imaging method of claim 2, wherein the number of angles for projection collection is larger than 8.

5. The PET imaging method of claim 2, wherein the coded aperture mask is designed by using a No-Two-Hole-Touching modified uniformly redundant array (NTHT MURA), a uniformly redundant array (URA), a random array or a pseudo random array.

6. The PET imaging method of claim 2, wherein a step of reconstructing the three-dimensional image in step 2) comprises:

(A) performing, by the computer imaging system, operations in steps a) and b) on each of the collected projection images:
    a) generation of a quasi three-dimensional image comprising: dividing, by the computer imaging system, the detected object into n layers, wherein n≥3, and z denotes a distance from each layer to the detector; and acquiring, by the computer imaging system, a quasi three-dimensional image of the detected object by using an iterative algorithm according to the n layers of the detected object;
    b) generation of a secondary projection image comprising: adjusting, by the computer imaging system, image pixels on each layer to the same size by interpolation and generating the secondary projection image, wherein the image on each layer after adjustment is denoted by $f_{(1)}(x, y, z)$; the secondary projection image is denoted by $p_{(2)}(x, y)$, wherein the function is obtained by using the formula $p_{(2)}(x, y)=\Sigma_z f_{(1)}(x, y, z)$;
(B) generating, by the computer imaging system, a sonogram comprising: extracting corresponding rows of each cross section from each secondary projection image, and generating the sinogram by arrangement according to the collection angles; and
(C) generating, by the computer imaging system, a full three-dimensional image comprising: reconstructing, by the computer imaging system, a tomographical image for each cross section from each sinogram.

7. The PET imaging method of claim 6, wherein the iterative algorithm in step a) is:

$$\hat{f}^{(k+1)}(x, y, z) = \frac{\hat{f}^{(k)}(x, y, z)}{\sum_z h(x, y, z)} \left\{ h(x, y, z) \otimes \frac{p(x, y) - \sum_{z' \neq z}\left[\hat{f}^{(k)}(x, y, z) * h(x, y, z)\right]}{\hat{f}^{(k)}(x, y, z) * h(x, y, z)} \right\},$$

wherein k denotes the number of iterations, $\hat{f}^{(k)}(x, y, z)$ denotes the $k^{th}$ estimation of the detected object, h (x, y, z) denotes a coded aperture mask shadow corresponding to an object at a depth of z, z denotes the distance from the detector to each layer, z denotes a distance from another layer (not layer z) to the detector, $\otimes$ denotes a correlation operation, and * denotes a convolution operation.

8. The PET imaging method of claim 6, wherein the tomographical image is reconstructed from each sinogram by using ordered subset expectation maximization (OSEM), filter back-projection, maximum likelihood expectation maximization (MLEM), or algebraic reconstruction technique.

9. The PET imaging method of claim 1, wherein the number of pinholes on the multi-pinhole plate is larger than 10.

10. The PET imaging method of claim 1, wherein the number of angles for projection collection is larger than 8.

11. A positron emission tomography (PET) imaging system, comprising: a computer imaging system, a device carrying a detected object, and a detector system disposed around the detected object for collecting gamma photons emitted in a positron annihilation event; wherein the detected object is traced by a radioactive isotope of β+ decay, and a multi-pinhole plate is disposed between the detected object and a detector;

wherein the detector is configured to collect gamma photon projections from a plurality of angles through the multi-pinhole plate; and the computer imaging system is configured to generate a projection image which is denoted by p(x, y), wherein x and y denote a coordinate of two dimensions of the detector, and a value of p represents photon counts detected by that detector individually without coincidence via a time coupling electronic circuit; and reconstruct a three-dimensional image based on all the projection images;

wherein the PET system does not include the time coupling electronic circuit, and the multi-pinhole plate is configured to collimate gamma photons, which allows an image to be acquired by detecting gamma photons emitted from annihilations without requirement to detect another photon coincident in time via the time coupling electronic circuit.

12. The PET imaging system of claim 11, wherein the detector synchronously rotates with the multi-pinhole plate.

13. The PET imaging system of claim 12, wherein the radius r of the pinholes on the multi-pinhole plate is from 1.25 mm to 8 mm, and the length t of the pinholes is from 3 mm to 20 mm.

14. The PET imaging system of claim 12, wherein the multi-pinhole plate is made of a heavy metal or heavy metals.

15. The PET imaging system of claim 11, wherein the multi-pinhole plate is a planar plate having a plurality of coded apertures, wherein a location of the coded apertures on the multi-pinhole plate is denoted by a matrix function h(x, y);

the detector rotates or is disposed at different angles to detect projections from a plurality of angles; and the computer imaging system is configured to reconstruct a three-dimensional image based on the projections collected by the detector.

16. The PET imaging system of claim 11, wherein the radius r of the pinholes on the multi-pinhole plate is from 1.25 mm to 8 mm, and the length t of the pinholes is from 3 mm to 20 mm.

17. The PET imaging system of claim 11, wherein the detector is made of bismuth germanate (BGO), sodium iodide (NaI) or cesium iodide (CsI).

18. The PET imaging system of claim 11, wherein the multi-pinhole plate is made of a heavy metal or heavy metals.

* * * * *